(12) United States Patent
Asfora

(10) Patent No.: US 6,923,799 B1
(45) Date of Patent: Aug. 2, 2005

(54) SUBDURAL EVACUATING PORT SYSTEM

(76) Inventor: Wilson T. Asfora, 1210 W. 18th St., Suite 104, Sioux Falls, SD (US) 57104-4614

( * ) Notice: Subject to any disclaimer, the term of this patent is extended or adjusted under 35 U.S.C. 154(b) by 104 days.

(21) Appl. No.: 10/205,990

(22) Filed: Jul. 26, 2002

Related U.S. Application Data

(60) Division of application No. 09/633,573, filed on Aug. 4, 2000, which is a continuation-in-part of application No. 29/105,951, filed on Jun. 4, 1999, now Pat. No. Des. 435,291.

(51) Int. Cl.$^7$ .............................................. A61M 1/00
(52) U.S. Cl. ................................................... 604/541
(58) Field of Search .............................. 604/19, 27, 28, 604/35, 37, 506, 73, 75, 93.01, 93.04, 540, 604/541, 317, 327, 355

(56) References Cited

U.S. PATENT DOCUMENTS 3,766,910 A * 10/1973 Lake ........................... 600/213
4,114,603 A    9/1978 Wilkinson (Continued)

OTHER PUBLICATIONS

Printout of Premarket Notification (510(k)) fro Medical Devicses from U.S. Food and Drug Administration website for (510(k) No. K974726.

(Continued)

Primary Examiner—L. I. Schwartz
Assistant Examiner—Michael Bogart
(74) Attorney, Agent, or Firm—Leonard & Proehl, Prof. L.L.C.; Jeffrey A. Proehl

(57) ABSTRACT

A subdural evacuating port system for removing subdural fluid accumulations in a manner that is minimally invasive and promotes decompression, expansion and recovery of the brain. The system includes a subdural evacuating port device including a tubular portion for partial insertion into an opening in a skull of a patient. The tubular portion has a proximal end and a distal end and a lumen extending between the proximal and distal ends. The port device has a pair of wings for facilitating finger rotation of the tubular portion, with the wings extending outwardly from the tubular portion in substantially opposite directions from the tubular portion. The exterior surface of the tubular portion may have self-tapping threads at the proximal end and may have a plurality of annular barbs at the distal end. A kit for evacuating a collection of fluid from a subdural space may include the subdural evacuating port device and a retractor for spacing sides of an incision in a scalp away from each other. The kit may include a drill bit and a stop collar selectively lockable in a position on the drill bit. A method of evacuating a fluid collection from a subdural space includes penetrating the skull to form an opening in the skull, providing the subdural evacuating port device, introducing the proximal end of the subdural evacuating port device into the opening, and creating a substantially uniform negative pressure condition in the subdural space of the patient through the subdural evacuating port device.

21 Claims, 4 Drawing Sheets

U.S. PATENT DOCUMENTS

| | | | |
|---|---|---|---|
| 4,438,773 A | | 3/1984 | Letterio |
| 4,446,715 A | | 5/1984 | Bailey |
| 4,572,212 A | | 2/1986 | Letterio |
| D283,053 S | | 3/1986 | Hermann |
| 4,578,057 A | * | 3/1986 | Sussman .................. 604/9 |
| 4,600,013 A | * | 7/1986 | Landy et al. ............ 600/561 |
| D285,112 S | | 8/1986 | Sato et al. |
| 4,621,647 A | | 11/1986 | Loveland |
| 4,677,985 A | | 7/1987 | Bro et al. |
| 4,705,047 A | | 11/1987 | Bailey |
| 4,828,546 A | * | 5/1989 | McNeil et al. ............ 604/73 |
| 4,838,264 A | * | 6/1989 | Bremer et al. .......... 606/104 |
| 4,858,619 A | | 8/1989 | Toth |
| 4,903,707 A | | 2/1990 | Knute et al. |
| 4,931,049 A | | 6/1990 | Klimas |
| 5,054,497 A | | 10/1991 | Kapp et al. |
| 5,107,847 A | | 4/1992 | Knute et al. |
| 5,117,836 A | | 6/1992 | Millar |
| 5,191,898 A | | 3/1993 | Millar |
| 5,203,770 A | * | 4/1993 | Wigness et al. ......... 604/506 |
| 5,330,501 A | * | 7/1994 | Tovey et al. ............ 606/198 |
| 5,348,048 A | * | 9/1994 | Schirado et al. ......... 137/588 |
| 5,372,583 A | * | 12/1994 | Roberts et al. ......... 604/506 |
| 5,387,222 A | * | 2/1995 | Strickland ............... 606/167 |
| 5,520,698 A | * | 5/1996 | Koh ........................ 606/119 |
| 5,562,688 A | * | 10/1996 | Riza ........................ 606/148 |
| 5,579,774 A | | 12/1996 | Miller et al. |
| 5,683,357 A | | 11/1997 | Magram |
| 5,707,373 A | * | 1/1998 | Sevrain et al. ............ 606/72 |
| 5,776,144 A | * | 7/1998 | Leysieffer et al. ....... 606/130 |
| 5,871,487 A | * | 2/1999 | Warner et al. .......... 606/130 |
| 5,913,852 A | | 6/1999 | Magram |
| 5,954,687 A | * | 9/1999 | Baudino .................. 604/48 |
| 6,110,155 A | * | 8/2000 | Baudino ................ 604/265 |
| D435,291 S | * | 12/2000 | Asfora .................. D24/129 |
| 6,210,346 B1 | * | 4/2001 | Hall et al. .............. 600/561 |
| 6,290,694 B1 | * | 9/2001 | Harper et al. .......... 604/540 |
| 6,350,233 B1 | * | 2/2002 | Lubowski ............... 600/158 |
| 6,391,017 B2 | * | 5/2002 | Bays ...................... 604/506 |

OTHER PUBLICATIONS

Printout of Premarket Notification (510(k)) fro Medical Devicses from U.S. Food and Drug Administration website for (510(k) No. K970578.

Printout of Premarket Notification (510(k)) fro Medical Devicses from U.S. Food and Drug Administration website for (510(k) No. K984053.

Printout of Premarket Notification (510(k)) fro Medical Devicses from U.S. Food and Drug Administration website for (510(k) No. K981046.

Printout of Premarket Notification (510(k)) fro Medical Devicses from U.S. Food and Drug Administration website for (510(k) No. K982702.

Printout of Premarket Notification (510(k)) fro Medical Devicses from U.S. Food and Drug Administration website for (510(k) No. K962928.

Printout of Premarket Notification (510(k)) fro Medical Devicses from U.S. Food and Drug Administration website for (510(k) No. K981846.

Copies from "Neurological and Neurosurgical Intensive Care", Third Edition. The article title is "Intracranial Pressure Monitoring Devices: Principles, Insertion, and Care". Consisting of pp. 53-68. Dated 1993. Published by Raven Press, Ltd., 1185 Avenue of the Americans, New York, NY 10036.

Nico Emonds and Werner E. Hassler. "New Device to Treat Chronic Subdural Hematoma-hollow Screw", Neurological Research, vol. 21 (Jan. 1999) pp. 77-78.

* cited by examiner

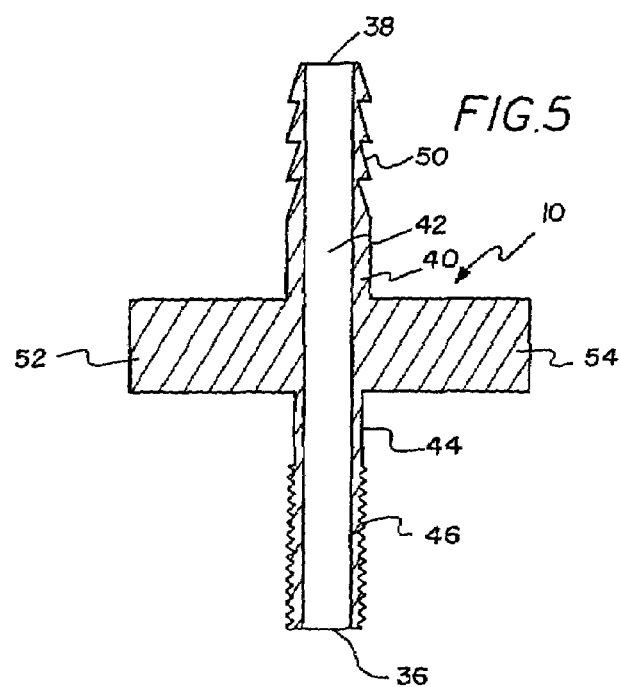
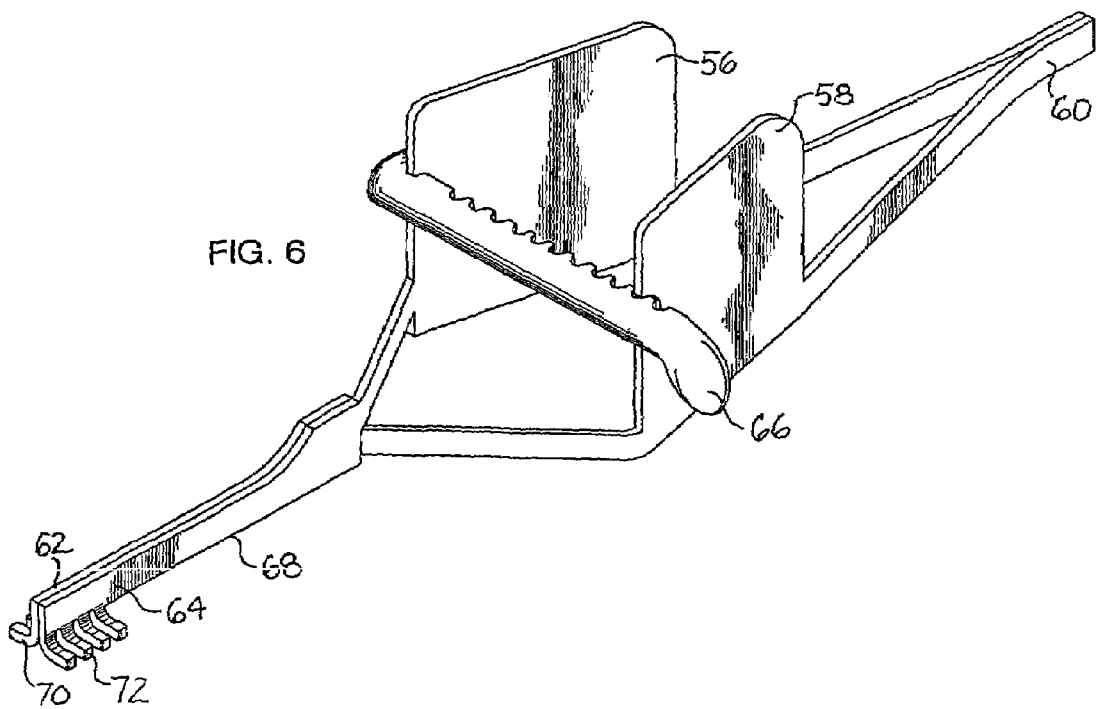

SUBDURAL EVACUATING PORT SYSTEM

CROSS REFERENCE TO RELATED APPLICATIONS

This application is a divisional of application Ser. No. 09/633,573, Aug. 4, 2000 which is a continuation-in-part of Application No. 29/105,951, filed Jun. 4, 1999 now U.S. Pat. No. D435,291.

BACKGROUND OF THE INVENTION

1. Field of the Invention

The present invention relates to systems for removing fluids from the subdural region of a patient and more particularly pertains to a new subdural evacuating port system for removing subdural fluid accumulations in a manner that is minimally invasive and promotes decompression, expansion, and recovery of the brain.

2. Description of the Prior Art

The subdural space of the human head is the space located between the brain and the lining of the brain, which is referred to as the dura mater (hereinafter referred to as the "dura"). Hemorrhages on the surface of the brain, for example, may cause a condition known as a subdural hematoma. The subdural hemorrhages may have a number of causes. For example, elderly persons may be more susceptible to subdural hemorrhages because as the brain ages it tends to become atrophic and the subdural space between the brain and the dura gradually enlarges. Bridging veins between brain and dura frequently stretch and rupture as a consequence of relatively minor head injuries, thus giving rise to a collection of blood in the subdural space. Further, severe linear deceleration of the brain can result in the brain moving excessively with respect to the dura, often causing rupture of the bridging veins or the blood vessels on the surface of the brain, which can in turn cause subdural hemorrhages in the "normal", young, and otherwise healthy brain.

These subdural blood collections can be classified as acute subdural hematomas, subacute subdural hematomas, and chronic subdural hematomas. Acute subdural hematomas, which are associated with major cerebral trauma, generally consist primarily of fresh blood. Subacute subdural hematomas are generally associated with less severe injuries than those underlying the acute subdural hematomas. Chronic subdural hematomas are generally associated with even less severe, or relatively minor, injuries. The chronic subdural hematomas tend to be less dense liquid consisting of very diluted blood.

Another condition involving a subdural collection of fluid is a hygroma, which is a collection of cerebrospinal fluid (sometimes mixed with blood) beneath the dura, usually in an encapsulation or cyst.

One form of treatment for acute subdural hematomas is the performance of a craniotomy operation. This operation entails the removal (with eventual replacement) of a large portion of the skull, opening of the dura, and evacuation of the collection of blood. The craniotomy frequently necessitates the placement of a subdural drain, which comprises a tube extending through the hole created by the crainiotomy and into the subdural space for removing any additional accumulation of blood or fluid. The craniotomy is a highly invasive procedure that generally involves significant risk to the patient and an extended recovery period.

Since the subacute and chronic types of subdural hematomas primarily comprise collections of liquid, the treatment may range from the performance of a craniotomy to the use of a burr hole. The burr hole operation generally comprises boring in the skull a hole that is smaller than the portion of skull removed in a craniotomy. The burr hole generally has a diameter of about 14 to 18 mm. Through the burr hole, extensive washing of the subdural space may be carried out. Frequently, a drain needs to be left in place through the burr hole, with the end of the drain being in communication with the surface of the brain in order to allow for postoperative drainage of any further accumulations of fluid. Again, the patient is exposed to a fairly invasive procedure and a relatively long recovery period.

The aforementioned drains are typically used in combination with the application of negative pressure through the tube of the drain. The typical level of the negative pressure applied by the drains frequently causes further hemorrhage of the brain, especially if the end of the tube should come in contact with the surface of the brain. Further, recurrence of subdural hematomas and hygromas is quite common in chronic cases as the brain generally fails to expand to fill the enlarged subdural space created by the collection of fluid. If the subdural space remains enlarged after removal of the fluid, additional fluid tends to collect in the enlarged subdural space. The aforementioned treatment techniques do not actively contribute to re-expansion of the brain within the dura, and therefore do little to prevent the re-accumulation of fluid in the enlarged subdural space.

The subdural evacuating port system according to the present invention substantially departs from the conventional concepts and designs and methods of the prior art, and in so doing provides an apparatus and method primarily developed for the purpose of removing subdural fluid accumulations in a manner that is minimally invasive and promotes decompression, expansion, and recovery of the brain.

SUMMARY OF THE INVENTION

In view of the foregoing disadvantages inherent in the known techniques and systems for removing fluids from the subdural region of a patient now present in the prior art, the present invention provides a new subdural evacuating port system with a device and method of use wherein the same can be utilized for removing subdural fluid accumulations in a manner that is minimally invasive and promotes the decompression, expansion, and recovery of the brain.

The invention includes a procedure for treating substantially liquid subdural fluid collections in a manner that is minimally invasive and does not involve touching the brain. Significantly, the procedure of the invention promotes brain expansion within the dura by creating a homogeneous, negative pressure throughout the subdural space from which the fluid collection has been removed.

The invention is especially effective when used on patients having a subdural space filled with fluid that is substantially liquid without significant coagulation of the fluid, including acute patients that are taking anticoagulants to enhance the fluidity of the matter that has accumulated in the subdural space.

The present invention generally comprises a subdural evacuating port device including a tubular portion for partial insertion into an opening in a skull of a patient. The tubular portion has a proximal end and a distal end and a lumen extending between the proximal and distal ends. The port device has a pair of wings for facilitating finger rotation of the tubular portion, with the wings extending outwardly from the tubular portion in substantially opposite directions from the tubular portion. The exterior surface of the tubular portion may have self-tapping threads at the proximal end and may have a plurality of annular barbs at the distal end. A kit for evacuating a collection of fluid from a subdural space may include the subdural evacuating port device and a retractor for spacing sides of an incision in a scalp away from each other. The kit may include a drill bit and a stop collar selectively lockable in a position on the drill bit. A method of evacuating a fluid collection from a subdural space includes penetrating the skull to form an opening in the skull, providing the subdural evacuating port device, introducing the proximal end of the subdural evacuating port device into the opening, and creating a substantially uniform negative pressure condition in the subdural space of the patient through the subdural evacuating port device.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is a schematic sectional view of subdural evacuating port device of the present invention.

FIG. 6 is a schematic side view of a retractor useful in the techniques of the present invention.

DESCRIPTION OF THE PREFERRED EMBODIMENT

Figure 1:
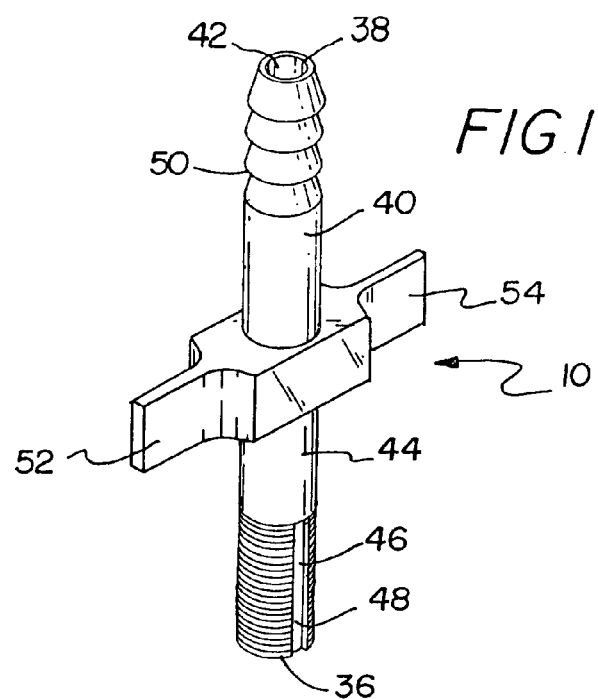
FIG. 1 is a schematic perspective view of a new subdural evacuating port device of the system of the present invention.
Figure 2:
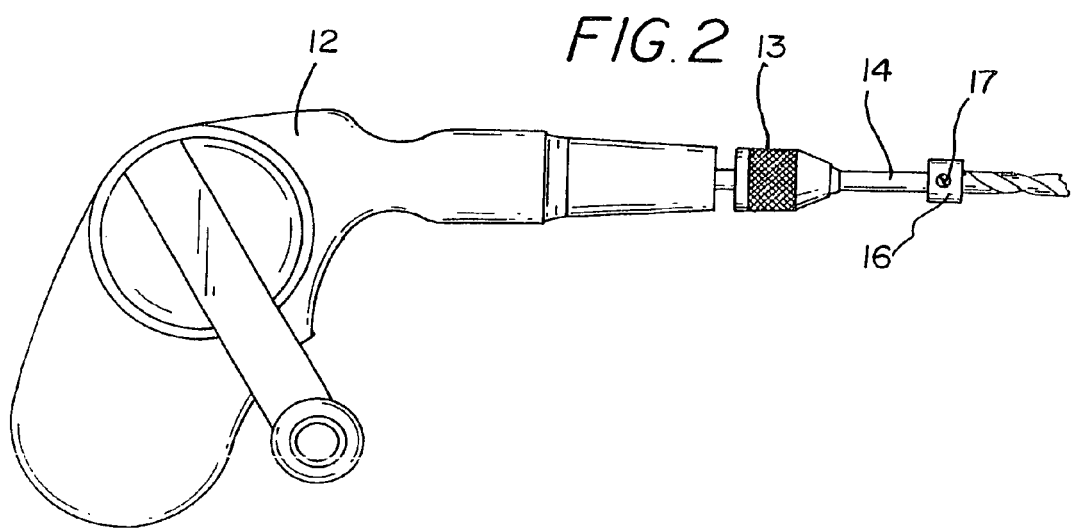
FIG. 2 is a schematic side view of a drill and bit useful in the techniques of the present invention.

With reference now to the drawings, and in particular to FIGS. 1 through 7 thereof, a new subdural evacuating port system embodying the principles and concepts of the present invention will be described.

As best illustrated in FIGS. 1 through 7, the system of the invention generally includes a subdural evacuating port device 10, and contemplates a kit for evacuating a collection of fluid from a subdural space of a patient that incorporates the subdural evacuating port device. The system also contemplates a method for utilizing the subdural evacuating port device and elements of the kit for removing fluid from the subdural space while facilitating the recovery of the patient's brain.

Elements useful in practicing the invention include the subdural evacuating port device 10, a drill device 12, a drill bit 14 for mounting on the drill device, a stop collar 16 for mounting on the drill bit, a retractor device 18, a negative pressure source 20, and a conduit 22.

The drill device 12 is provided for rotating the drill bit 14. The drill bit is mountable on the drill device in a suitable manner, such as by an adjustable chuck assembly 13. The chuck assembly 13 of the drill device 12 is most preferably rotated by manual means (e.g., turned by the surgeon's hand), but optionally the chuck assembly may be driven by motorized means.

The drill bit 14 is adapted for removably mounting on the drill device 12, and the drill bit 14 is preferably sized for creating a opening of a suitable size in the skull of the patient, as will be discussed in greater detail below. Illustratively, the drill bit 14 is formed of a stainless steel material.

The stop collar 16 is preferably provided for selectively limiting the maximum penetration of the tip of the drill bit 14 into the skull of the patient. The stop collar 16 is most preferably selectively lockable in a variety of longitudinal positions along the length of the drill bit 14 depending upon the depth of penetration needed to produce an opening through the skull without injuring the brain. The stop collar 16 is provided with a channel for receiving a portion of the drill bit 14, and the stop collar has a set screw 17 for extending into the channel and abutting against the drill bit 14 for locking the stop collar in a selected longitudinal position. Illustratively, one suitable material for the stop is a nylon, such as DELRIN.

The retractor device 18 is provided for holding back the edges of an incision made through the scalp of the patient. The retractor device 18 is especially useful for reducing the possibility of contact between the drill bit and the scalp when the drill bit is inserted through the incision for boring into the skull, and thus reduces any damage resulting from such contact. Preferably, the retraction device is of the type known as an "Holzheimer" retractor (see FIG. 6). The "Holzheimer" retractor generally has two arms 56, 58 that are joined together at proximal ends of the arms to form an apex 60. The arms 56, 58 extend away from the apex 60 and terminate at free ends 62, 64 of the arms. Preferably, the free ends of the arms are spaced such that the arms form a substantially V-shaped structure. A locking member 66 may be included on the retractor for selectively locking the arms at a desired spacing. The "Holzheimer" retractor 18 has a lower edge 68 for inserting into the incision. A tab 70, 72 may be provided on each of the arms 56, 58 adjacent to the lower edge 68 at a location separated from the apex 60 of the clip. The tabs 70, 72 preferably lodge themselves below the outer surface of the scalp to help hold the clip in place with respect to the incision during the period when the incision needs to be held open. Optionally, but less preferably, retraction of the scalp may be performed by other known types of surgical retractors, such as, for example, a "Mastoid" retractor, a "Gelpi" retractor, or a "Heiss" retractor.

The negative pressure device 20 is provided for creating a uniform negative pressure condition in the subdural space of the patient. The negative pressure device exerts a suction for imparting a uniform partial vacuum in the subdural space. Importantly, the magnitude of the negative pressure condition created is relatively low for exerting a gentle suction in the subdural space. The substantial uniformity of the negative pressure is considered important for promoting the gradual re-expansion of the brain in the subdural space. The magnitude of the negative pressure exerted by a suitable negative pressure source is approximately 0.8 inch to 1 inch of mercury (Hg) with respect to atmospheric pressure. It will be appreciated that a lower level (e.g., less than 0.8 inches of mercury) of negative pressure may be used, although the effectiveness of the fluid removal will be reduced. While relatively higher levels of negative pressure may be used (such as up to approximately 1.2 inches of mercury), significantly higher levels of negative pressure can hamper the recovery of the brain and the associated tissues, by, for example, not allowing the brain to fully re-expand to its condition prior to the fluid accumulating in the subdural space. The relatively low level of negative pressure permits the negative pressure condition to be maintained in the subdural space for a relatively extended period of time for removing any further collection of fluid, as well as promoting a gradual expansion of the brain in the subdural space during the healing process.

Figure 3:
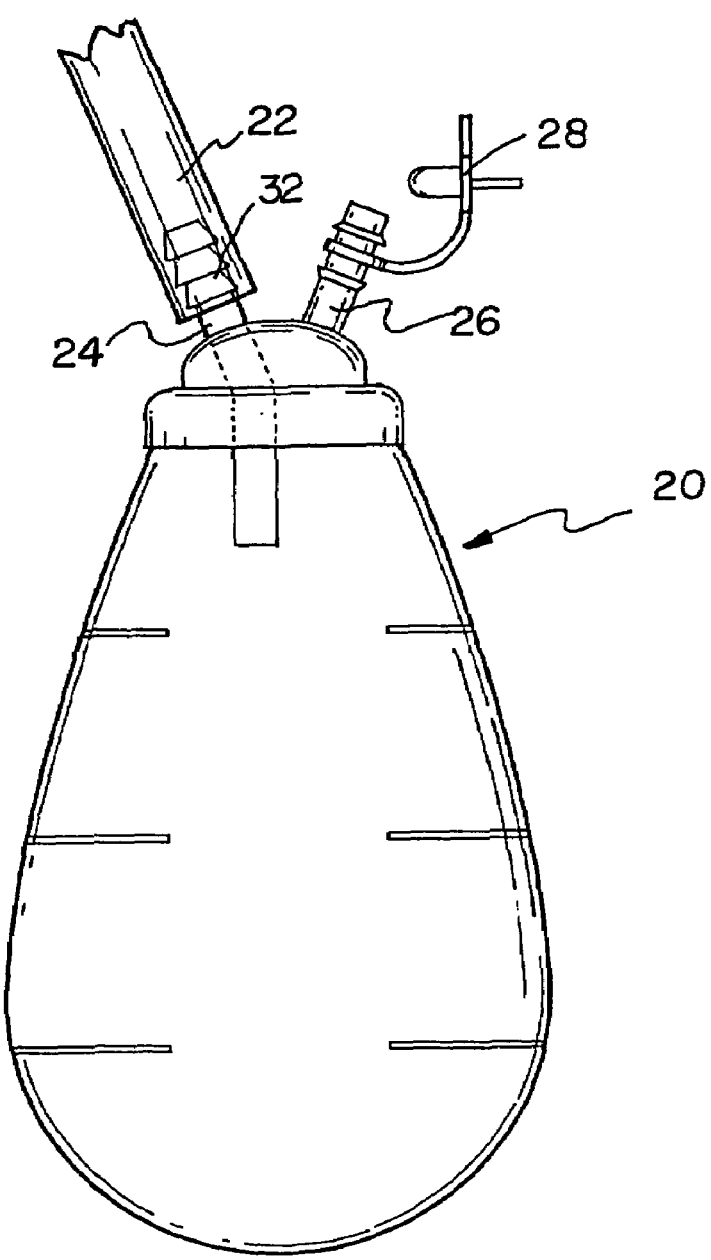
FIG. 3 is a schematic side view of a bulb useful in the techniques of the present invention.
Figure 4:
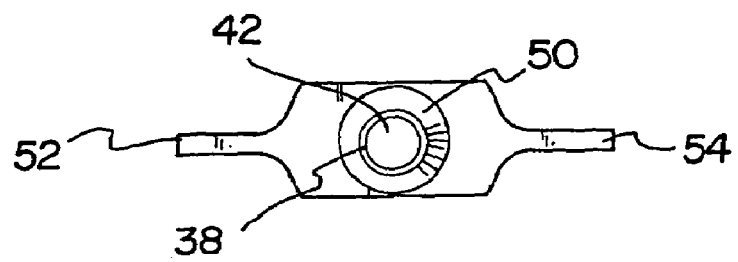
FIG. 4 is a schematic end view of the subdural evacuating port device of the present invention.
Figure 7:
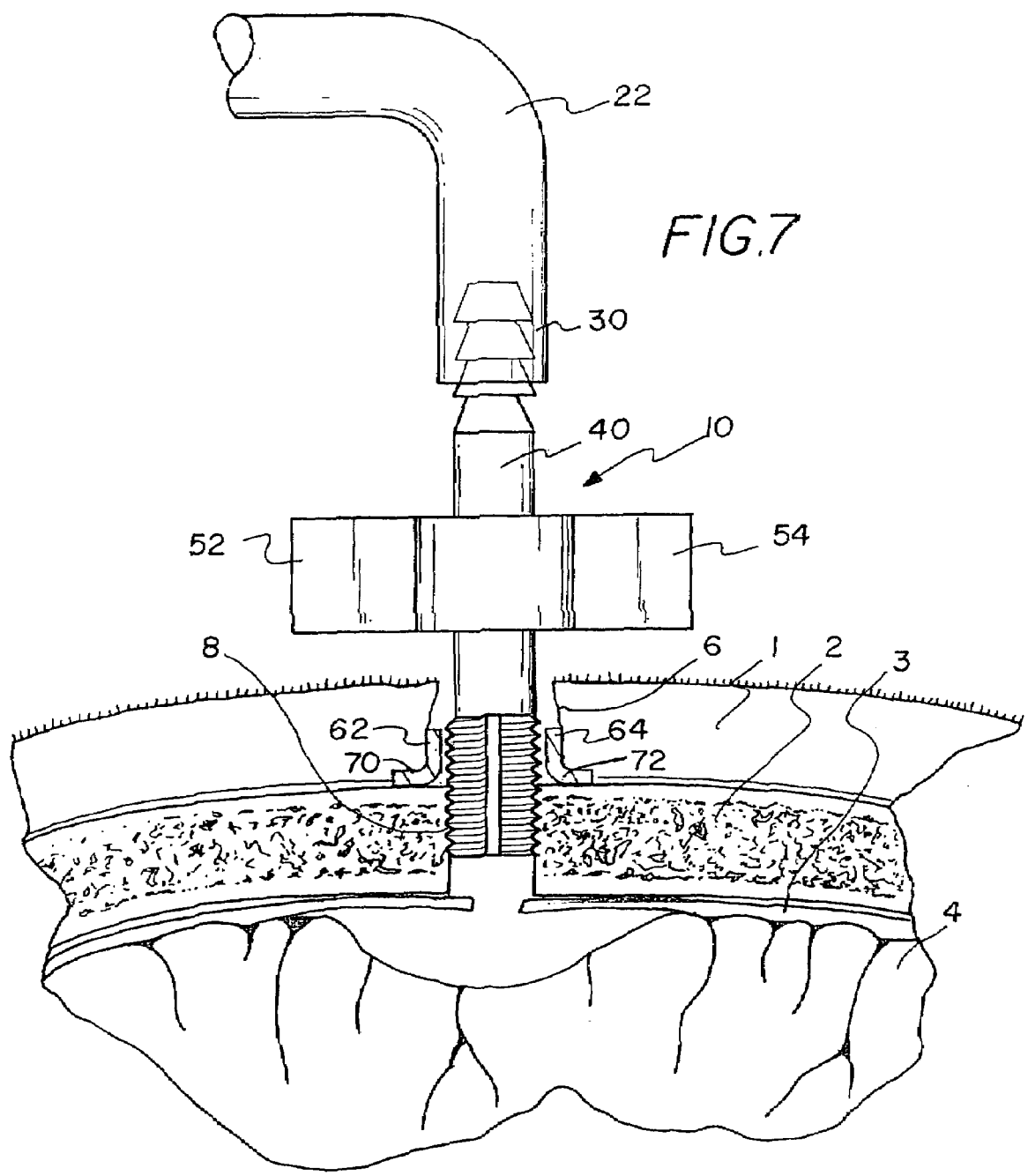
FIG. 7 is a schematic sectional view of a portion of a patient's skull and brain area with the subdural evacuating port device mounted on the skull.

A highly preferable negative pressure source is a device commonly referred to as a Jackson-Pratt bulb (see FIG. 3). The Jackson-Pratt bulb 20 has an interior and a pair of openings 24, 26. More particularly, the bulb 20 has a primary opening 24 and a secondary opening 26, and each opening extends between the interior and an exterior of the bulb. A check valve (not shown) is provided on the bulb 20 in communication with the primary opening 24 for resisting exit of fluid (e.g., gas or liquid) from the interior to the exterior of the bulb through the primary opening while permitting fluid flow into the interior through the primary opening. A cap 28 may be provided for selectively closing the secondary opening 26 of the bulb thus requiring any fluid entering the interior to enter through the primary opening 24.

The conduit 22 may be provided for fluidly connecting the subdural evacuating port device 10 with the negative pressure source. Preferably, the conduit 22 connects the primary opening 24 of the Jackson-Pratt bulb 20 with the subdural evacuating port device. The conduit 22 has first 30 and second 32 ends, and the first end 30 is removably connectable to the subdural evacuating port device 10 and the second end 32 is removably connectable to the primary opening 24 of the Jackson-Pratt bulb 20. The conduit may comprise flexible tubing of the type commonly used for draining fluids from the body, such as, for example, tubing formed from a silicone material. Illustratively, a length of tubing between approximately 2½ and 3 feet (approximately 75 cm and 90 cm) is suitable.

A highly significant feature of the invention is the subdural evacuating port device 10 for penetrating the skull of the patient. The port device 10 includes a substantially tubular portion 40 with a lumen 42 that extends between a proximal end 36 and a distal end 38 of the port device. An exterior surface 44 of the proximal end 36 of the tubular portion is preferably provided with self-tapping threads 46 formed thereon for cutting threads into the skull of the patient as the proximal end is inserted into a opening 8 in the patient's skull 2 and the port device is rotated in the opening. Illustratively, a longitudinal groove 48 may extend through the self-tapping threads 46 to produce thread cutting surfaces on the exterior surface 44. An exterior surface 44 of the distal end 38 of the tubular portion 40 preferably has a plurality of annular barbs 50 formed thereon for retaining the conduit 22 on the distal end 38.

Significantly, the subdural evacuating port device 10 includes a pair of wings 52, 54 extending outwardly from the tubular portion 40 which facilitate finger rotation of the tubular portion in the opening 8 of the skull 2 during the threading of the opening by the self-tapping threads 46 of the port device. Preferably, the wings 52, 54 extend in substantially opposite directions for enhancing finger grippability of the wings. The wings 52, 54 may be mounted on the tubular portion at a location substantially medially between the proximal 36 and distal 38 ends of the tubular portion 40, between the self-tapping threads 46 and the annular barbs 50.

In one illustrative and highly preferred embodiment of the port device, the diameter of the exterior surface of the tubular portion measures approximately 6 mm. The lumen has a diameter of approximately 3.8 mm. The length of the tubular portion from the distal end to the proximal portion is approximately 45 mm. The width between the tips of the wings is approximately 23 mm, and the width of the wings is approximately 5 mm. The self-tapping threads extend approximately 10 mm from the proximal end, and the annular barbs extend approximately 15 mm from the distal end.

The method aspect of the invention permits evacuation of a collection of fluid from the subdural space within the skull 2 of a patient. One of the initial acts of the method includes determining the region of the scalp 1 of the patient that is adjacent to the location of the collection of fluid in the subdural space. Preferably, the region is located on the patient's scalp 1 where the collection of fluid has the greatest dimension or measurement in the subdural space of the skull. The location of the greatest dimension of the fluid collection may be determined by performing an imaging study of the head of the patient using, for example, computerized tomography or magnetic resonance imaging to determine the extent of the collection of fluid. Once the greatest dimension of the collection of fluid is determined, the location of the opening to be made through the skull to the subdural cavity is selected on the scalp at a substantially central location corresponding to the greatest dimension of the collection of fluid.

The scalp 1 of the patient may be infiltrated with an anesthetic such as by injecting the anesthetic into the scalp in the region where the subdural collection of fluid has the greatest dimension. Illustratively, the anesthetic may be lidocaine or epinephrine, or other suitable anesthetic.

An incision 6 is created in the scalp 1 to expose the bone of the skull 2 of the patient. The incision 6 extends through the scalp 1, the subcutaneous tissue, the galea, and the periosteum. The retractor device 18 is introduced into the incision 6 for holding the scalp 1 adjacent to the incision away from the operating area.

An opening 8 is created in the skull 2 of the patient using the drill bit 14 mounted in the drill device 12. Preferably, the size of the opening 8 formed in the skull may be approximately 3 to 8 mm in diameter. Most preferably, the opening 8 in the skull is approximately 5 to 7 mm in diameter. Ideally, the appropriate size opening is approximately 6 mm in diameter. The size of the drill bit 14 is such that it will create a suitable size opening in the skull.

The dura 3 may then be penetrated by incising the dura of the patient using, for example, a unipolar cautery device. The underlying membranes may be transected with the unipolar cautery device.

Fluid that has collected in the subdural space is removed from the space through the incision in the dura 3. This removal is most preferably performed through the use of the subdural evacuating port device 10. The proximal end 36 of the subdural evacuating port device is introduced into the opening 8 in the skull 2. The port device 10 is rotated in the opening 8 such that the self-tapping threads 46 engage the sides of the opening and pull the proximal end 36 into the opening and secure the port device against unintentional withdrawal of the device from the opening. The dura 3 may be penetrated by the proximal end 36 of the port device 10 for placing the lumen 42 in fluid communication with the subdural area, and any collection of fluid in a subdural space.

A substantially uniform negative pressure condition is created in the subdural space. This negative pressure condition is most preferably created through the lumen 42 of the subdural evacuating port device 10 of the invention. The first end 30 of the conduit 22 is connected to the distal end 38 of the subdural evacuating port device, with the annular barbs 50 retaining the conduit on the port device. The second end 32 of the conduit 22 is connected to the negative pressure source. The primary opening 24 of a Jackson-Pratt bulb 20 is connected to the second end 32 of the conduit 22. To produce the negative pressure condition in the conduit 22 and the lumen 42 of the port device 10, the Jackson-Pratt bulb 20 is compressed (such as by hand gripping of the bulb) with the cap 28 removed from the secondary opening 26 to expel as much air from the bulb as possible. The cap 28 is then placed over the secondary opening 26, and the expansion of the resilient bulb from the collapsed condition produces a negative pressure condition in the interior of the bulb as well as the conduit 22 and the lumen 42 of the port device 10.

The negative pressure condition created in the lumen 42 of the port device 10 tends to draw fluid collected in the subdural space through the lumen and into the conduit 22 and into the interior of the bulb. The fluid collected in the interior of the bulb may be periodically emptied from the bulb, and the negative pressure condition may be reapplied to the subdural space through the port device using the bulb.

The negative pressure condition may be removed when drainage from the subdural space is no longer observed, or the desired re-expansion of the brain in the subdural space has occurred, or as is determined to be medically advisable. To remove the subdural evacuating port device 10, the device is rotated (e.g., using the wings 52, 54) such that the threads 46 move the port device out of the opening 8.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A method of evacuating a collection of fluid from a subdural space within the skull of a patient, comprising the acts of:
    forming an opening in the skull;
    providing a subdural evacuating port device having a proximal end and a distal end;
    introducing the proximal end of the subdural evacuating port device into the opening in the skull and into communication with the subdural space; and
    creating a substantially uniform negative pressure condition in the subdural space of the patient through the subdural evacuating port device.

2. The method of claim 1 additionally comprising determining the region of the scalp where the collection of fluid in the subdural space has a greatest dimension measured along the surface of the scalp.

3. The method of claim 2 wherein the act of determining includes performing an imaging study of the skull of the patient using computerized tomography imaging to determine the extent of the collection of fluid.

4. The method of claim 1 additionally comprising infiltrating the scalp of the patient with an anesthetic by injecting the anesthetic into the scalp.

5. The method of claim 1 additionally comprising creating an incision in the scalp of the patient to expose the skull of the patient.

6. The method of claim 5 additionally comprising retracting portions of the scalp adjacent to the incision away from each other.

7. The method of claim 5 additionally comprising introducing a retractor into the incision.

8. The method of claim 1 wherein the act of forming an opening includes drilling a hole in the skull.

9. The method of claim 8 wherein the act of drilling the hole includes providing a drill bit having a diameter of approximately 6 mm.

10. The method of claim 1 additionally comprising penetrating a dura by incising the dura of the patient with a unipolar cautery.

11. The method of claim 1 wherein the act of providing the subdural evacuating port device includes forming a tubular portion of the subdural evacuating port device with a lumen extending between the proximal and distal ends, and forming a pair of wings on an exterior surface of the tubular portion of the port device, the wings extending outwardly in opposite directions from the tubular portion.

12. The method of claim 11 wherein the act of providing the subdural evacuating port device includes forming self-tapping threads on an exterior surface on the tubular portion at the proximal, and forming a plurality of annular barbs on the exterior surface on the tubular portion at the distal end.

13. The method of claim 12 additionally comprising rotating the proximal end of the subdural evacuating port device in the opening so that the self-tapping threads engage the opening.

14. The method of claim 1 additionally comprising penetrating a dura of the patient with the proximal end of the subdural evacuating port device.

15. The method of claim 1 additionally comprising connecting a first end of a conduit to the distal end of the subdural evacuating port device and connecting a second end of the conduit to a negative pressure source.

16. The method of claim 1 wherein the act of creating a negative pressure condition includes providing a negative pressure source in communication with the subdural space of the patient through the subdural evacuating port device.

17. The method of claim 16 wherein the act of providing a negative pressure condition includes connecting a suction bulb to the subdural evacuating port device.

18. The method of claim 17 additionally comprising compressing the bulb and closing a secondary opening of the bulb by placing a cap on the secondary opening.

19. The method of claim 17 additionally comprising emptying the bulb as fluid accumulates in the bulb.

20. The method of claim 17 additionally comprising removing the negative pressure condition from the subdural space when drainage from the subdural space through the subdural evacuating port device into the bulb is no longer observed.

21. The method of claim 1 wherein the step of introducing the proximal end of the subdural evacuating port device includes positioning the proximal end of the subdural evacuating port device in the subdural space between the dura of the patient and the arachnoid of the patient.

* * * * *